Figure 1:
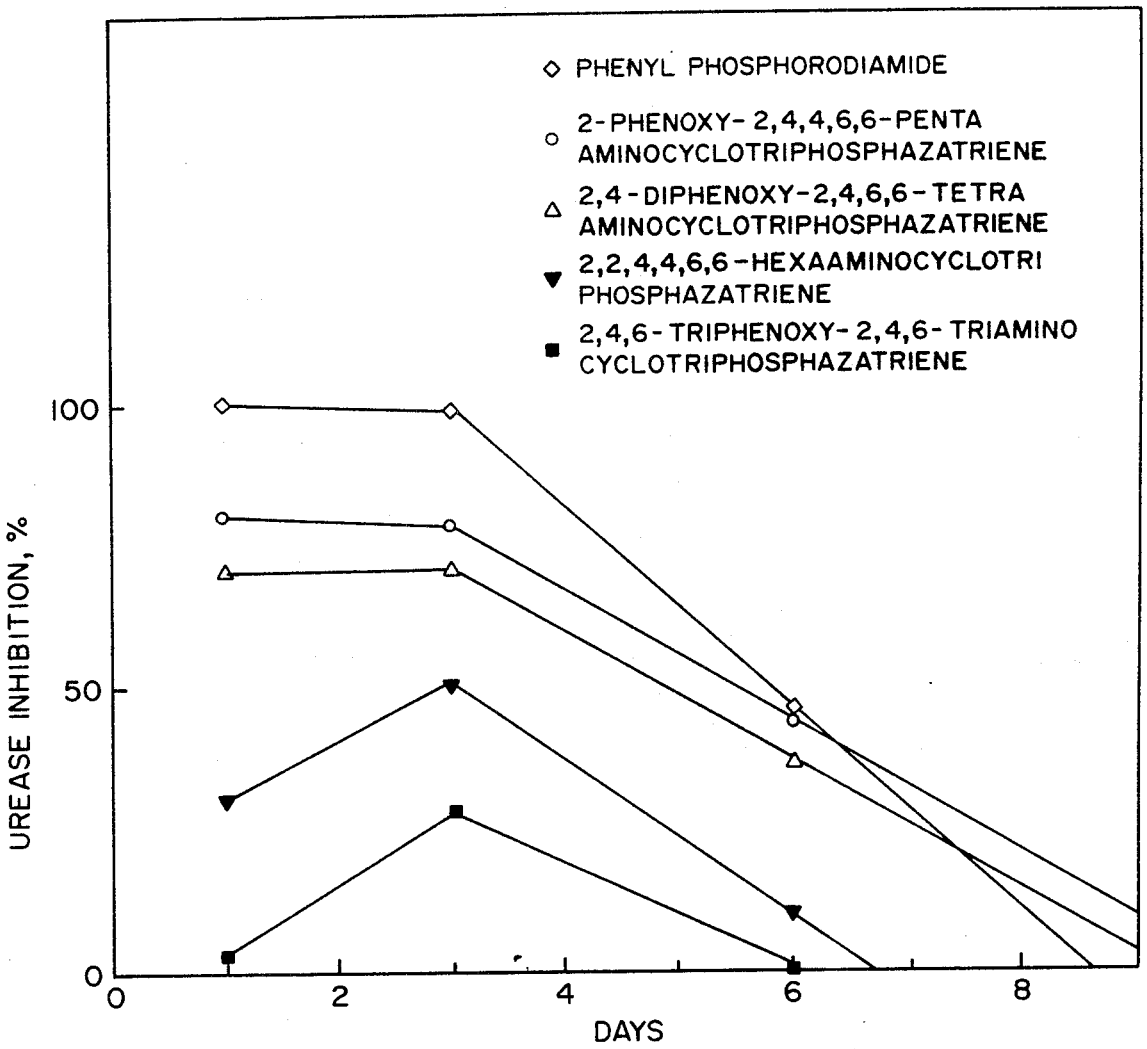
Figure 2:
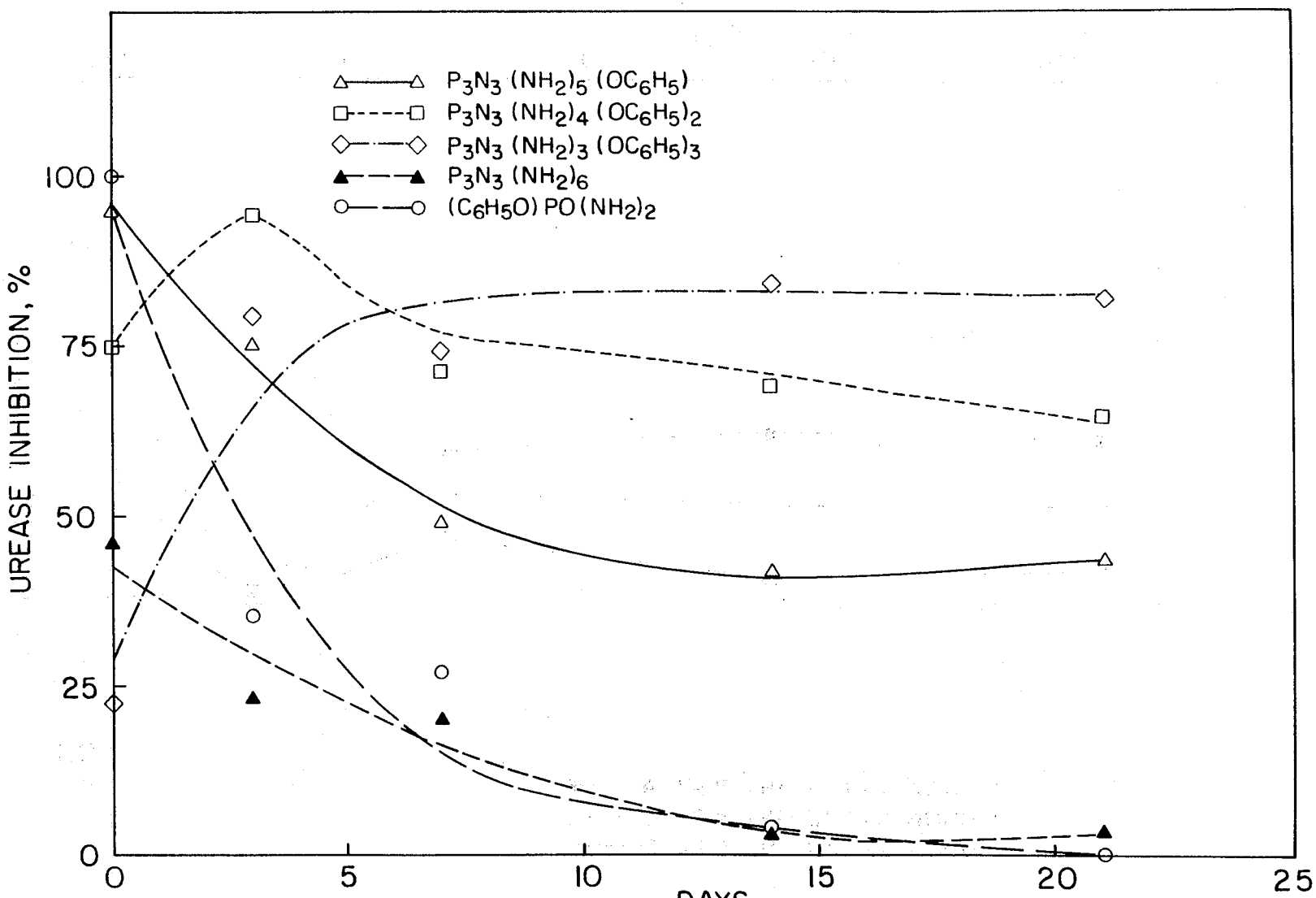
Figure 3:
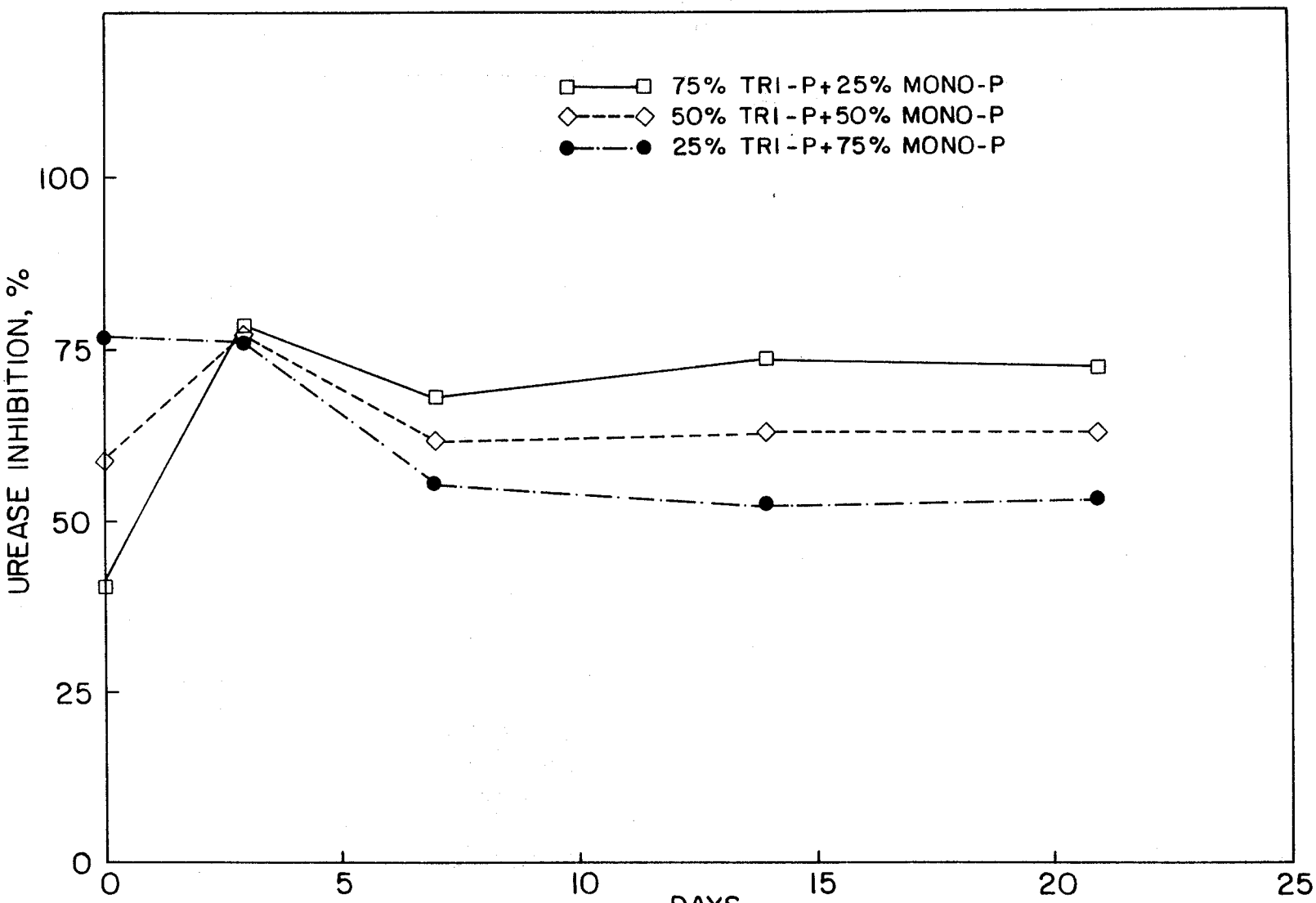
Figure 4:
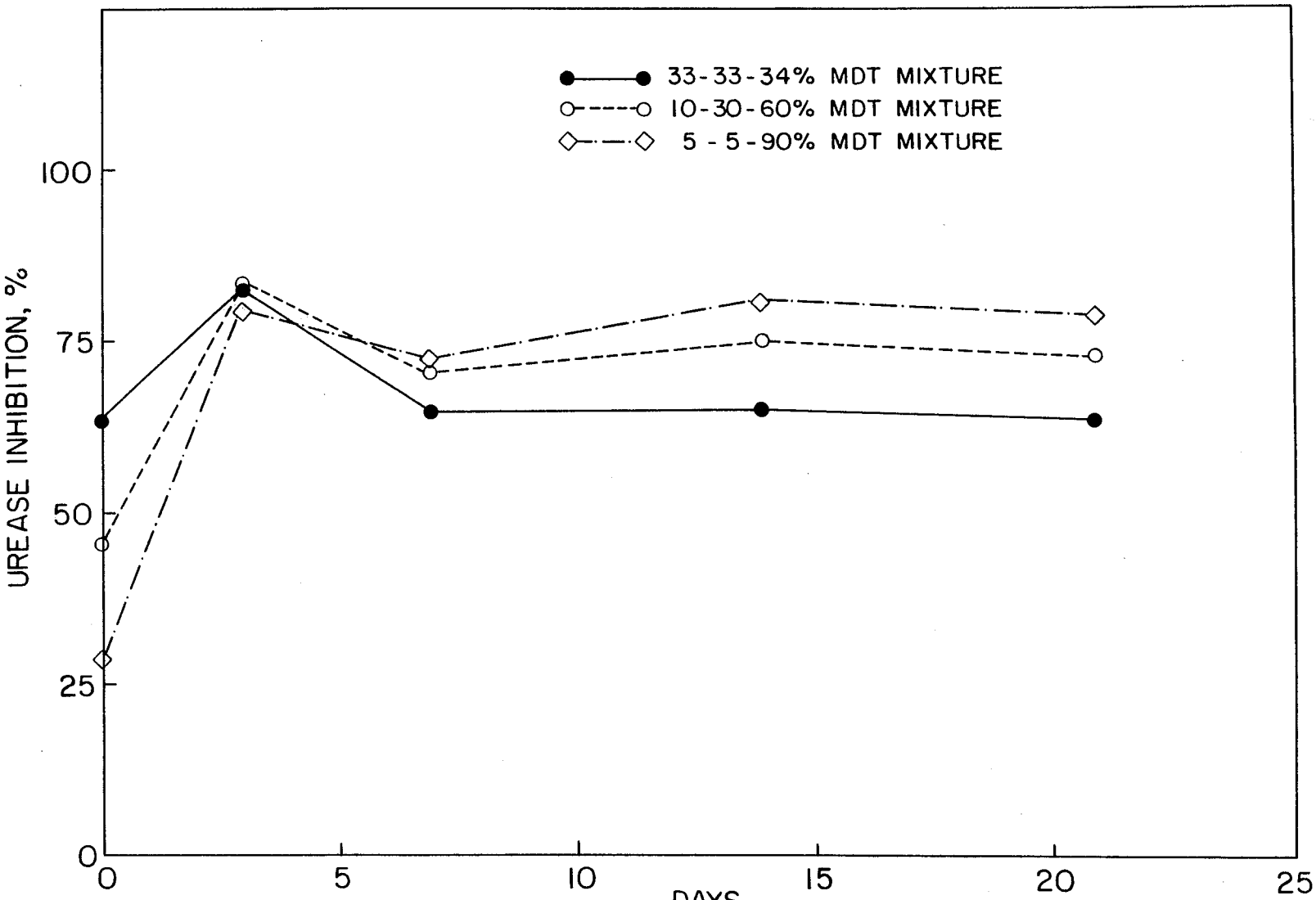

United States Defensive Publication [19] (H) [11] T105,605

Medina et al. [43] Jul. 2, 1985

[54] CYCLOTRIPHOSPHAZATRIENE-DERIVATIVES AS SOIL UREASE ACTIVITY INHIBITORS

[76] Inventors: Ramiro Medina, 105 Fountain St., Sheffield, Ala. 35660; Jack M. Sullivan, 106 Patsy Dr., Florence, Ala. 35630

[21] Appl. No.: 625,424

[22] Filed: Jun. 28, 1984

[51] Int. Cl.[3] ..... C12P 3/00; C07F 9/22; C07F 9/24

[52] U.S. Cl. ..... 435/168; 435/227; 260/927 N; 423/302

[57] ABSTRACT

Tests show that 2,2,4,4,6,6-hexaaminocyclotriphosphazatriene, 2-phenoxy-2,4,4,6,6-pentaaminocyclotriphosphazatriene, 2,4-diphenoxy-2,4,6,6-tetraaminocyclotriphosphazatriene and 2,4,6-triphenoxy-2,4,6-triaminocyclotriphosphazatriene (also frequently called phosphonitrilic derivatives) of the formula

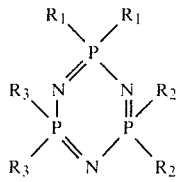

are highly effective inhibitors of urease activity in agricultural soil systems wherein (1) $R_1 \ldots R_3' = NH_2$ or (2) $R_1' = R_2' = R_3' = R_2 = R_3 = NH_2$ and $R_1 = OC_6H_5$ or (3) $R_1' = R_2' = R_3' = R_3 = NH_2$ and $R_1 = R_2 = OC_6H_5$ or (4) $R_1' = R_2' = R_3' = NH_2$ and $R_1 = R_2 = R_3 = OC_6H_5$ The above-mentioned compounds and mixtures of the compounds show sustained inhibition of the soil urease activity for periods of at least 21 days.

25 Claims, 4 Sheets Drawing,

40 Pages Specification

The file of this unexamined application may be inspected and copies thereof may be purchased (849 O.G. 1221, Apr. 9, 1968).